United States Patent [19]
Yao et al.

[11] Patent Number: 5,242,814
[45] Date of Patent: Sep. 7, 1993

[54] POLYETHER ANTIBIOTIC

[75] Inventors: Raymond C. Yao, Carmel; Robert L. Hamill, Greenwood, both of Ind.

[73] Assignee: Eli Lilly and Company, Indianapolis, Ind.

[21] Appl. No.: 706,901

[22] Filed: May 29, 1991

Related U.S. Application Data

[62] Division of Ser. No. 420,508, Oct. 10, 1989, Pat. No. 5,043,353.

[51] Int. Cl.$^5$ .................... C12P 19/60; C12P 17/16; C12P 17/18; C12R 1/55
[52] U.S. Cl. .................... 435/75; 435/118; 435/119; 435/898
[58] Field of Search .................... 435/76, 75, 118, 119, 435/898

[56] References Cited

U.S. PATENT DOCUMENTS

| | | | |
|---|---|---|---|
| 3,705,238 | 12/1972 | Hamill et al. | 424/121 |
| 3,839,557 | 10/1974 | Raun et al. | 424/115 |
| 3,839,558 | 10/1974 | Hamill et al. | 424/121 |
| 3,950,514 | 4/1976 | Sawada et al. | 424/121 |
| 4,069,316 | 1/1978 | Imada et al. | 424/122 |
| 4,133,876 | 1/1979 | Hamill et al. | 424/121 |
| 4,138,481 | 2/1979 | Martin et al. | 424/181 |
| 4,148,881 | 4/1979 | Ishiguro | 424/120 |
| 4,148,882 | 4/1979 | Celmer et al. | 424/122 |
| 4,218,438 | 8/1980 | Callender et al. | 424/115 |
| 4,278,663 | 7/1981 | Liu et al. | 424/119 |
| 4,293,650 | 10/1981 | Florent et al. | 435/119 |
| 4,366,168 | 12/1982 | Clinton et al. | 424/283 |
| 4,552,843 | 11/1985 | Celmer et al. | 435/76 |
| 4,565,862 | 1/1986 | Foley et al. | 536/16.8 |
| 4,582,822 | 4/1986 | Hamill et al. | 514/25 |
| 4,628,046 | 12/1986 | Labeda et al. | 514/33 |
| 4,764,534 | 8/1988 | Clinon et al. | 514/657 |
| 5,015,578 | 5/1991 | Schroeder et al. | 435/76 |

FOREIGN PATENT DOCUMENTS

314330A2 5/1989 European Pat. Off. .
317231A2 5/1989 European Pat. Off. .

OTHER PUBLICATIONS

Derwent Publications Ltd. Abstract No. 60613B/33 of Japanese Patent 4084-576 to Kaken Chem. KK.
"Polyether Antibiotics, Naturally Occurring Acid Ionophores, vol. 1, Biology", John W. Westley Ed., Marcel Dekker, Inc., New York, 1982, pp. 1-20.
Yohko Kusakabe, et al., "Antibiotic No. 6016, A Polyether Antibiotic," *Journal of Antibiotics,* vol. XXXIII, No. 12, pp. 1437-1442 (1980).
R. S. Wehbie, et al., "The Antibiotic W341C, Its Ion Transport Properties and Inhibitory Effects on Mitochondrial Substrate Oxidation," *Journal of Antibiotics,* vol. XL, No. 6, pp. 887-893 (1987).

*Primary Examiner*—Jerome D. Goldberg
*Attorney, Agent, or Firm*—James P. Leeds; Leroy Whitaker

[57] ABSTRACT

New polyether antibiotic A80789, its acyl ester, alkyl ester, and alkyl ether derivatives, and salts thereof, are useful as antibacterial and anticoccidial agents and increase feed-utilization efficiency in animals. Methods of making A80789 by culture of *Streptomyces hygroscopicus* NRRL 18513, and combinations of the A80789 compounds with nicarbazin, 4,4'-dinitrocarbanilide, certain napthalenamine and benzenamine compounds and are also provided.

5 Claims, 3 Drawing Sheets

POLYETHER ANTIBIOTIC

This application is a division of application Ser. No. 07/420,508, now U.S. Pat. No. 5,043,353, filed Oct. 10, 1989.

BACKGROUND OF THE INVENTION

Animal health products are in great demand. Antibiotics continue to be an important type of animal health product, not only for treating disease, but also for enhancing growth promotion in animals. Antibiotics can promote growth by reducing disease or by increasing feed-utilization efficiency.

One disease which has a serious impact on the poultry industry is coccidiosis. Coccidiosis results from infection by one or more species of Eimeria or Isospora. Improved anticoccidial agents are in demand because of the continuing economic losses due to coccidiosis.

Promoting growth by increasing feed-utilization efficiency is another economically desirable objective of veterinary science. This type of growth promotion is particularly important for ruminants, such as cattle, and for monogastric animals such as poultry and swine.

One group of antibiotics which has been especially important in the animal health field are the polyether antibiotics. For example, the polyether monensin is a valuable commercial product; it is used both for treating coccidiosis in poultry and for increasing feed-utilization efficiency in animals.

Antibiotic A80789 ("A80789") is a member of the group of polyether antibiotics. Westley (John W. Westley, "Polyether Antibiotics: Naturally Occurring Acid Ionophores, Vol. 1, Biology," Marcel Dekker: New York, 1982) has separated existing polyethers by class and type. Using Westley's system, A80789 is a member of the Class 1b, type (1), group of polyethers because it has one spiroketal system. Other members of this group include A80190 (U.S. Pat. No. 4,582,822); A-28695 A and B (U.S. Pat. No. 3,839,558); A204 I and II (U.S. Pat. No. 3,705,238); A-32887 (U.S. Pat. No. 4,133,876); carriomycin; etheromycin; CP-47,434; RP37454 and the X-14868 antibiotics.

SUMMARY OF THE INVENTION

This invention relates to a new polyether antibiotic A80789, which is produced by *Streptomyces hygroscopicus*, NRRL 18513. The structure of A80789 is shown in formula 1:

This invention also relates to the acyl ester, alkyl ether and alkyl ester derivatives of A80789 and to the salts thereof. Antibiotic A80789 has an acid function capable of forming salt and ester derivatives and has at least one hydroxyl group which can be esterified or which can form ether derivatives. The acyl ester, alkyl ether, and alkyl ester derivatives of A80789 and the pharmaceutically acceptable salts thereof are also useful as antibiotics and as agents which increase feed-utilization efficiency. In addition, A80789 has insecticidal and antiviral activity.

The term "acyl ester derivative" means a derivative of A80789 wherein a hydrogen atom of one of the hydroxyl groups is replaced by a $C_2$ to $C_7$ alkanoyl group.

The term "alkyl ether derivative" means a derivative of A80789 wherein one or more of the hydroxyl groups has been replaced by a YR group wherein: Y represents O or S; and R represents $C_1$ to $C_6$ alkyl or phenyl-$C_1$ to $C_3$ alkyl.

The term "alkyl ester derivative" means a derivative of A80789 wherein the hydroxy of the carboxyl group is replaced by a $C_1$ to $C_6$ alkoxy group.

The term "A80789 compound" is used to designate antibiotic A80789 (formula 1), an acyl ester derivative, an alkyl ester derivative, an alkyl ether derivative, or a salt thereof.

Another aspect of this invention relates to the compositions and combinations of A80789 compounds for use as antibiotics and as agents which increase feed-utilization efficiency. A composition is an A80789 compound mixed with a physiologically acceptable carrier. A combination means a composition wherein an A80789 compound is combined with a compound selected from the group consisting of a) nicarbazin,
b) 4,4-dinitrocarbanilide,
c) a naphthalenamine compound of formula 2:

wherein:
$R^2$ is $C_1$-$C_4$ alkyl;
$R^3$ is halogen, $C_1$-$C_4$ fluoroalkyl, $C_1$-$C_4$ fluoroalkoxy or $C_1$-$C_4$ fluoroalkylthio;
$R^4$ is halogen;
$R^5$ is hydrogen or halogen;
m is 0, 1 or 2; and
n is 0 or 1;

with the proviso that, when an $R^4$ substituent exists, it is at other than the 2-position;

d) a benzenamine selected from 2,4-dinitro-N-[4-(trifluoromethoxy)phenyl]-6-(trifluoromethyl)benzenamine, 2,4-dinitro-N-[4-(1,1,2,2-tetrafluoroethoxy)phenyl]-6-(trifluoromethyl)benzenamine or 2,4-dinitro-N-[4-(pentafluoroethoxy)phenyl]-6-(trifluoromethyl)benzenamine; or e) a pharmaceutically acceptable salt of a (b)–(d) compound.

Another aspect of this invention is the method of producing A80789 by culturing a strain of *Streptomyces hygroscopicus*, NRRL 18513, or an A80789-producing mutant thereof, under submerged aerobic conditions until a substantial level of the antibiotic is produced. A80789 is extracted from the fermentation broth and from the mycelium with polar organic solvents. A80789 is separated and further purified by techniques such as column chromatography.

Because *Streptomyces hygroscopicus* NRRL 18513 is a newly discovered strain, this invention further provides a biological purified culture of this microorganism.

DETAILED DESCRIPTION OF THE INVENTION

The term "alkyl" means a $C_1$ to $C_6$ straight or branched hydrocarbon, e.g., methyl, ethyl, propyl, isopropyl, n-butyl, s-butyl, t-butyl, pentyl, isopentyl, or hexyl. Preferably, the term "alkyl" means a $C_1$ to $C_4$ straight or branched hydrocarbon, e.g., methyl, ethyl, propyl, isopropyl, n-butyl, s-butyl, or t-butyl.

The terms "$C_1$ to $C_6$ alkoxy" and "$C_1$ to $C_3$ alkoxy" mean a $C_1$ to $C_6$ alkyl group, as defined supra, or a $C_1$ to $C_3$ alkyl group, respectively, attached to an oxygen atom. Preferably, the $C_1$ to $C_6$ alkoxy group includes: methoxy, ethoxy, propoxy, i-propoxy, butoxy, s-butoxy, t-butoxy, pentoxy, i-pentoxy, and hexoxy. Examples of the $C_1$ to $C_3$ alkoxy group are methoxy, ethoxy, propoxy, and i-propoxy.

The term "phenyl" means an aromatic group wherein one or more of the hydrogen atoms of a benzene ring may be substituted by $C_1$ to $C_2$ alkyl, e.g., 4-methylphenyl, 2-methylphenyl, 2,4-dimethylphenyl, or 3,4-dimethylphenyl; halo, e.g., 4-chlorophenyl, 4-bromophenyl, 2-chlorophenyl, 2-bromophenyl, 2,4-diclorophenyl, or 2,4-dibromophenyl; and $C_1$ to $C_3$ alkoxy, e.g., 4-methoxyphenyl, or 2-methoxyphenyl. A substituent is preferably on the 4-position, e.g., 4-chlorophenyl, 4-bromophenyl, 4-methylphenyl, or 4-methoxyphenyl.

The term "$C_2$ to $C_7$ alkanoyl group" includes straight or branched chain $C_1$ to $C_6$ alkyl groups, as defined supra, attached to a carbonyl group. Preferably, the alkyl group attached to the carbonyl is a $C_1$ to $C_3$ alkyl group. Examples of the preferred alkanoyl groups are acetyl, propionyl, n-butyryl, and s-butyryl.

Characteristics of A80789

Antibiotic A80789 has been assigned Structure 1 (based on mass spectrometry and NMR studies).

A80789 (in its free acid form) has the following characteristics:

State: White crystals

Mp: 115°–117° C. or 118°–120° C., varies with the degree of solvation

Molecular weight: 884 (field desorption mass spectrometry)

Empirical formula: $C_{47}H_{80}O_{15}$

UV: End absorption only

Figure 1:
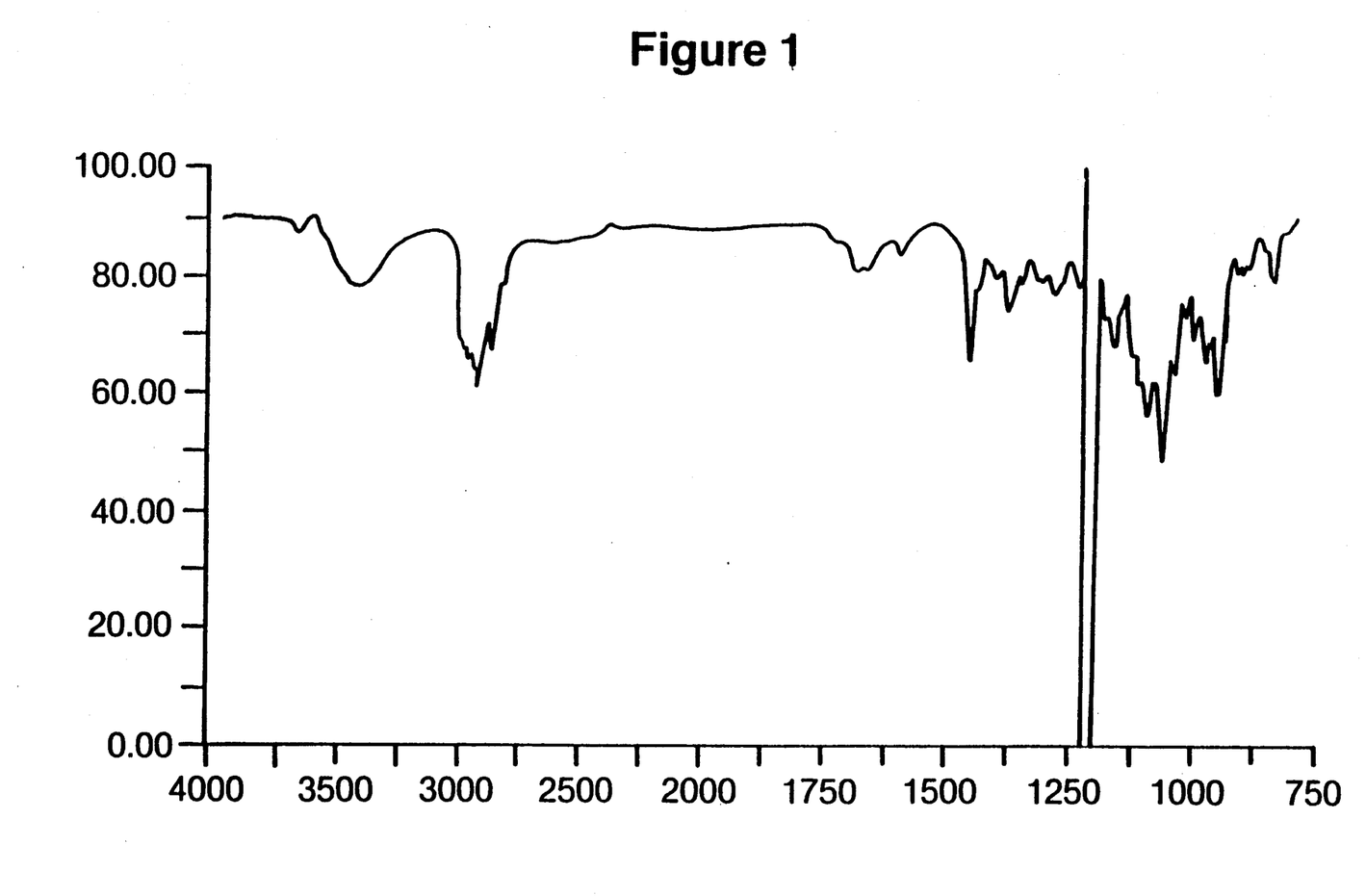
FIG. 1 shows the infrared absorption spectrum of A80789 in chloroform.
Figure 2:
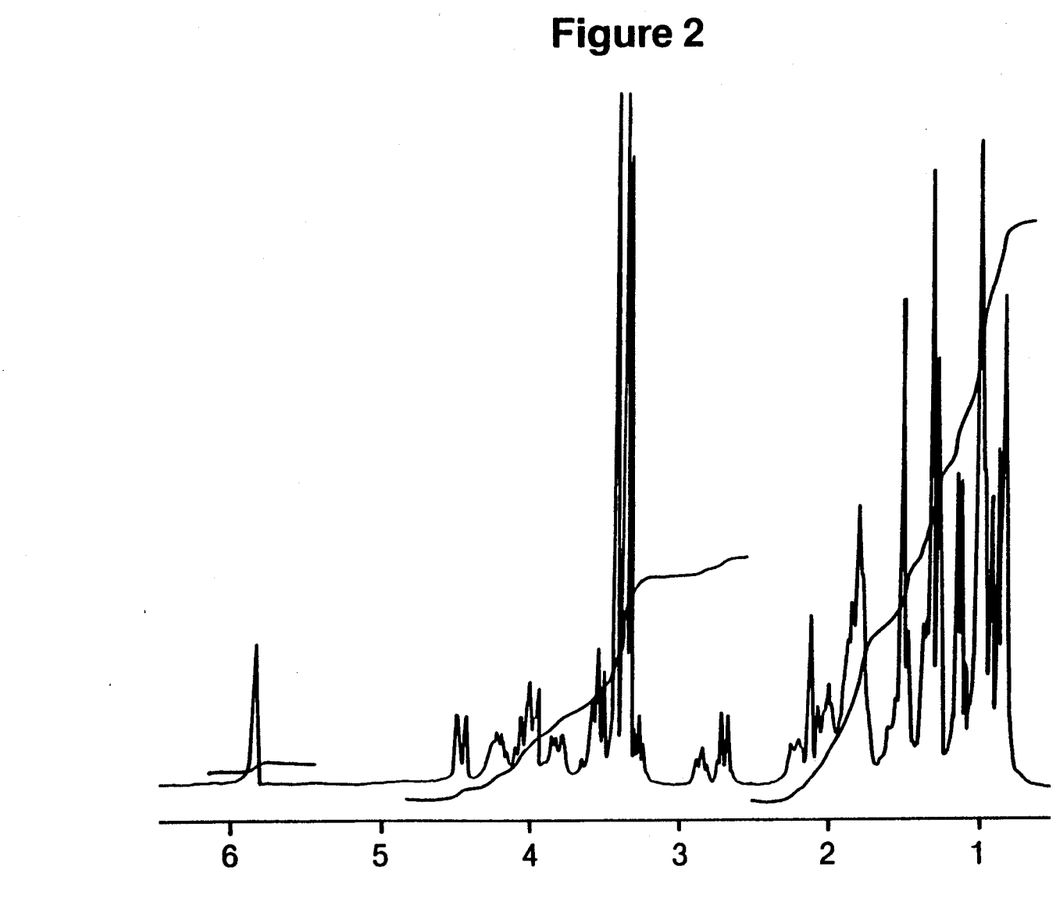
FIG. 2 shows the proton nuclear magnetic resonance spectrum of A80789 in deuterochloroform.

IR ($CHCl_3$): FIG. 1; shows absorption at the following frequencies ($cm^{-1}$): 3020, 2978, 2952, 2934, 2880, 1735, 1695, 1603, 1460, 1380, 1290, 1167, 1101, 1069, 1043, 1002, 983, and 955.

Solubility: Insoluble in water; soluble in lower alcohols such as methanol, ketones such as acetone, esters such as ethyl acetate, halogenated hydrocarbons such as chloroform and hydrocarbons such as diethyl ether, benzene, toluene, and warm hexane.

The new microorganism of this invention, which produces antibiotic A80789, is called culture A80789 for convenience. Culture A80789 was isolated from a soil sample from Manioka in New Guinea.

A culture of the A80789-producing organism has been deposited and made part of the stock culture collection of the Northern Regional Research Center, Agricultural Research, North Central Region, 1815 North University Street, Peoria, Ill., 61604, from which it is available to the public under the accession number NRRL 18513.

Taxonomic studies of culture A80789 show that the organism is a new strain of the genus Streptomyces for which the name *Streptomyces hygroscopicus* is proposed. This classification is based on laboratory comparison with similar species and comparison of culture A80789's characteristics with published descriptions of the characteristics of similar species.

Methods Used

These studies were made using methods recommended by the International Streptomyces Project (ISP) for the characterization of Streptomyces species [E. B. Shirling and D. Gottlieb, "Methods for Characterization of Streptomyces Species," *Int. J. Syst. Bacteriol.*, 16:313–340 (1966)].

Starch hydrolysis was determined by testing for the presence of starch with iodine on ISP No. 4 (inorganic salts-starch agar) plates.

NaCl tolerance was measured by adding NaCl to ISP No. 2 agar to equal the concentration desired.

ICSS-NBS Centroid Color Charts, standard sample No. 2106 (National Bureau of Standards, 1958, U. S. Department of Commerce, Washington, D.C.) and the Color Harmony Manual (4th ed., Container Corporation of America, Chicago, Ill., 1958) were used to assign color names to the reverse side and to aerial hyphae, respectively.

Morphology was studied using an optical light microscope. A scanning electron microscope (SEM) was used to study the spore surface ornamentation.

The isomers of diaminopimelic acid (DAP) and the carbohydrates in hydrolysates of whole cells were established by the chromatographic methods of Becker et al. [B. Becker, M. P. Lechevalier, R. E. Gordon, and H. E. Lechevalier, "Rapid Differentiation between Nocardia and Streptomyces by Paper Chromatography of Whole-cell Hydrolysates," *Appl. Microbiol.*, 12:421–423 (1964)] and Lechevalier [M. P. Lechevalier and H. E.

Lechevalier, "Chemical Composition as a Criterion in the Classification of Aerobic Actinomycetes," *Int. J. Syst. Bacteriol.*, 20:435-443 (1970)].

Resistance to antibiotics was measured by padding antibiotic sensitivity discs onto the surface of seeded ISP No. 2 agar plates. Resistance was scored as (+) when no zone of inhibition was observed and as (−) when a zone of inhibition was observed.

Melanoid pigment production (chromogenicity) was determined with ISP No. 1 (tryptone-yeast extract broth), ISP No. 6 (peptone-yeast extract iron agar), and ISP No. 7 (tyrosine agar).

Cultural Characteristics

Culture A80789 grew well on both complex and defined media. The color of the aerial spore mass varied from brown-gray to red-brown, and on some media was white. Moist black (hygroscopic) patches were observed on ISP Medium 3. The reverse side was yellow-brown. Soluble pigments were not observed. The cultural characteristics of culture A80789 are summarized in Table I.

Morphological Characteristics

Culture A80789 produces an extensive substrate mycelium. Aerial hyphae produce long, compact, nonsegmented spirals consisting of 3-5 coils. Their nonsegmented rugose spore surface is characteristic of a type I cell surface of *Streptomyces hygroscopicus* [A. Dietz and J. Mathews, "Taxonomy by Carbon Replication II. Examination of Eight Additional Cultures of *Streptomyces hygroscopicus*." *Appl. Microbiol.*, 16: 935-941 (1968)].

TABLE I

| Cultural characteristics of A80789 on Various Agar Media[a] | |
|---|---|
| Agar Media | A80789 Characteristics[b] |
| ISP No. 2 | G: Abundant |
| | R: 74.s.YBr |
| | Am: Good: 2b Pale Yellow |
| | Sp: None |
| ISP No. 3 | G: Abundant (moist patches) |
| | R: 110.gy.Olive |
| | Am: Good: 3ig gy.y.Br |
| | Sp: None |
| ISP No. 4 | G: Abundant |
| | R: 72.d.OY |
| | Am: Good: 5fe 1.gy.rBr |
| | Sp: None |
| ISP No. 5 | G: Good |
| | R: 72.d.OY |
| | Am: Fair: b White |
| | Sp: None |
| ISP No. 7 | G: Abundant |
| | R: 55.s.Brown |
| | Am: Good: 2dc y Gray |
| | Sp: Light-reddish brown |
| No. 172 | G: Good |
| | R: 90.Gy.Yellow |
| | Am: Good: b White |
| | Sp: None |
| Emerson's | G: Good |
| | R: 70.l.OY |
| | Am: Fair: a White |
| | Sp: None |
| Czapek's | G: Abundant |
| | R: 76.l.yBr |
| | Am: Fair: b White |
| | Sp: None |
| Tomato Paste Oatmeal | G: Good |
| | R: 77.m.yBr |
| | Am: Fair a White |
| | Sp: None |
| Potato Carrot | G: Good |
| | R: 87.m.Yellow |
| | Am: Fair b White |
| | Sp: None |
| Jensen's | G: Good |
| | R: 112.1.Olive Gray |
| | Am: Fair: 5fe 1.gy.rBr |
| | Sp: None |
| Glucose Asparagine | G: Good |
| | R: 90.gy.Yellow |
| | Am: Fair: a White |
| | Sp: None |
| Glycerol Glycine | G: Poor |
| | R: 88.d.Yellow |
| | Am: None |
| | Sp: None |
| Yeast Dextrose | G: Good |
| | R: 72.d.OY |
| | Am: Trace (edges): a White |
| | Sp: None |
| Calcium Malate | G: Fair |
| | R: 77.M.yBr |
| | Am: None |
| | Sp: None |

[a]When incubated at 30° C. for 18 days
[b]G=Growth
R=Reverse
Am=Aerial mycelium
Sp=Soluble Pigment

Physiological Characteristics

Culture A80789 utilized the following carbohydrates to produce acid: adonitol, arabinose, cellobiose, D-fructose, D-galactose, glucose, glycerol, glycogen, i-inositol, inulin, lactose, D-maltose, D-mannitol, D-mannose, D-melezitose, D-melibiose, raffinose, L-rhamnose, sodium butyrate, salicin, sucrose, D-trehalose and D-xylose. A80789 was unable to utilize: cellulose, dextrin, dulcitol, ethanol, i-erythritol, α-methyl-D-glucoside, D-ribose, sorbitol, L-sorbose, and xylitol.

Culture A80789 grew in a temperature range of 15°-37° C. An optimal growth temperature appeared to be 25° C. The culture tolerated levels of NaCl up to and including 5%.

Culture A80789 produced catalase and hydrolyzed starch. The culture did not reduce nitrate or produce melanoid pigment.

Culture A80789 was resistant to lincomycin (2 mcg), penicillin G (10 units), and rifampin (5 mcg). It was sensitive to bacitracin (10 units), cephalothin (30 mcg), gentamicin (10 mcg), neomycin (30 mcg), oleandomycin (15 mcg), streptomycin (10 mcg), tetracycline (30 mcg), tobramycin (10 mcg), and vancomycin (30 mcg).

Cell Wall Analyses

Hydrolyzed whole cells contained LL-diaminopimelic acid. No diagnostic sugars were detected in the whole cell extract. Thus, culture A80789 has a type I cell wall and a N.C. sugar pattern [see M. P. Lechevalier and H. Lechevalier, "Chemical Composition as a Criterium in the Classification of Aerobic Actinomycetes," *Int. J. Syst. Bacteriol.*, 20:435-443 (1970)].

Identity of Culture A80789

The chemotaxonomic properties and the general cultural and morphological characteristics of culture A80789, support the assignment of this strain to the genus Streptomyces. (see V. B. D. Skerman, V. McGowan, and P. H. A. Sneath, *Approved List of Bacterial Names*, American Society for Microbiology, Washington, D.C., 1980). A literature comparison of the characteristics of similar strains indicate that culture A80789 is most similar to, and has therefore been classified as, a strain of *Streptomyces hygroscopicus* (Jensen 1931) Waksman and Henrici 1948. The published characteristics of *S. hygroscopicus* and the characteristics of culture A80789 are compared in Table II.

TABLE II

| Comparison of A80789 and *S. hygroscopicus* | | |
|---|---|---|
| | A80789 | *S. hygroscopicus* |
| Aerial spore color | Gray | Gray |
| Reverse side color | Yellow brown | Yellow brown |
| Morphology | S | S |
| Spore chain length | Long coils | Long coils |
| Spore surface | Rugose | Rugose |
| Spore shape | Unsegmented | Unsegmented |
| Melanoid pigments | − | − |
| Carbon utilization: | | |
| glucose | + | + |
| arabinose | + | + |
| xylose | + | + |
| inositol | + | + |
| mannitol | + | + |
| fructose | + | + |
| rhamnose | + | + |
| sucrose | + | − |
| raffinose | + | − |
| galactose | + | + |
| salicin | + | + |
| sorbose | − | − |
| NaCl tolerance-% | 5 | 7 |
| Hygroscopic areas | + | + |
| Soluble pigments | − | − |

As is the case with other organisms, the characteristics of the A80789-producing culture of this invention, *Streptomyces hygroscopicus* NRRL 18513, are subject to variation. Mutants of the strain may be obtained by methods known in the art, for example, by treatment with various physical and chemical mutagens such as ultraviolet light, X rays, gamma rays and chemicals such as N-methyl-N'-nitro-N-nitrosoguanidine. Natural and induced mutants of *Streptomyces hygroscopicus* NRRL 18513 which retain the characteristic of A80789 production are considered part of this invention.

Production of A80789

The culture medium used to grow the *Streptomyces hygroscopicus* culture can be any one of a number of media. For economy in production, optimal yield, and ease of product isolation, however, certain culture media are preferred. Thus, for example, a preferred carbon source in large-scale fermentation is glucose although xylose, galactose, mannose, mannitol, and the like can also be used.

A preferred nitrogen source is Bacto-peptone (Difco Laboratories, Detroit, Mich.), although enzyme-hydrolyzed casein, yeast, liver meal, meat peptones, fish meal, and the like are also useful. Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. Foaming is not usually a problem, but small amounts (i.e. 0.5 mL/L) of an anti-foam agent such as polypropylene glycol may be added to large scale fermentation media if needed.

For production of substantial quantities of antibiotic A80789, submerged aerobic fermentation in tanks is preferred. Small quantities of A80789 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A80789 is produced by the A80789-producing organism when grown at temperatures between about 15° C. and about 40° C. An optimum temperature for A80789 production appears to be about 30° C.

As is customary in submerged aerobic culture processes, sterile air is blown into the vessel from the bottom while the medium is stirred with conventional turbine impellors. The maximum oxygen uptake of the fermentation under the conditions used thus far has not exceeded about 0.2 mM/L/minute. In a fully baffled 165-liter fermentor containing approximately 110 liters of broth, an aeration rate of 0.125 v/v/m with an agitation rate of 300 rpm is sufficient to maintain the level of dissolved oxygen at or above 45% of air saturation at a pressure of 0.34 atmospheres.

Production of antibiotic A80789 can be followed during the fermentation by testing samples of the broth for antibiotic activity against organisms known to be sensitive to the antibiotic. One assay organism useful in testing A80789 is *Bacillus subtilis* ATCC 6633. The bioassay is conveniently performed by the agar-well diffusion test.

Following its production under submerged aerobic fermentation conditions, A80789 can be recovered from the fermentation medium by methods used in the fermentation art. The antibiotic activity produced during fermentation of the A80789-producing organism occurs both in the filtered broth and in the mycelial mass. Maximum recovery of A80789 is accomplished, however, by initially filtering the medium to separate the broth from the mycelial mass. The filtered broth and the mycelial mass can then be purified separately to give their respective portion of A80789. A variety of techniques may be used in this purification. A preferred technique for purification of the filtered broth requires adjusting it to a pH of about 9 and extracting with a suitable solvent such as, for example, ethyl acetate. The extracting solvent can then be evaporated under vacuum to give the broth portion of A80789.

A preferred method of purifying the mycelial mass is to extract the separated mycelial filter cake with a suitable solvent such as, for example, acetone. The extracting solvent is then evaporated under vacuum to give a concentrated aqueous solution. This aqueous solution is then adjusted to a pH of about 9 and is extracted with a suitable solvent such as, for example, ethyl acetate. The extracting solvent is then concentrated under vacuum to give the mycelial portion of A80789.

The broth and mycelial portions of A80789 are further purified by similar procedures. A preferred procedure involves silica-gel chromatography.

Alternatively, the culture solids, including medium constituents and mycelium, can be used without extraction or separation, but preferably after removal of water, as a source of A80789. For example, after production of A80789, the whole fermentation broth can be dried by lyophilization, by drum-drying, or by azeotropic distillation and drying. The dried broth is then mixed directly into feed premix.

A80789 Compounds

The salts of A80789 and of its derivatives are useful for separating and purifying the antibiotics. The pharmaceutically acceptable salts are particularly useful. However, nonpharmaceutically-acceptable salts may be useful in purification of an A80789 compound, e.g., crystallization.

When treating an animal, it is not ordinarily of great significance whether the free base or a salt of a compound or its derivative is used. A salt form may, however, be chosen for reasons of economy, convenience or toxicity.

The alkali-metal and alkaline-earth-metal cationic salts of A80789 are prepared according to procedures commonly used for the preparation of cationic salts. For example, the free acid of A80789 is dissolved in a suitable solvent such as acetone; a ⅓ volume of water is added; and this solution is adjusted to a pH of about 9 to 10 with the base of the desired cationic salt (e.g. NaOH, KOH). The salt thus formed can be isolated by routine methods, such as filtration or evaporation of the solvent.

A preferred method of forming salts is to dissolve A80789 (acid form) in a water-immiscible solvent such as ethyl acetate, add an equal volume of water, and adjust the mixture to pH 10 with the corresponding cationic base (e.g. NaOH, KOH, etc.) The separated organic phase is washed with water and concentrated to dryness. The residue is lyophilized from dioxane. The salt can be crystallized from an appropriate solvent mixture, such as acetone/water.

The salts formed with organic amines can be prepared similarly. For example, the gaseous or liquid amine can be added to a solution of A80789 in a suitable solvent such as acetone; the solvent and excess amine can be removed by evaporation.

Representative and suitable alkali-metal and alkaline-earth metal salts of A80789 include the sodium, potassium, lithium, cesium, rubidium, barium, calcium and magnesium salts.

Illustrative amine salts of A80789 include the ammonium and the primary, secondary, and tertiary $C_1$-$C_4$-alkylammonium and hydroxy-$C_2$-$C_4$-alkyl-ammonium salts. The preferred amine salts are those formed by reaction of A80789 with ammonium hydroxide, methylamine, sec-butylamine, isopropylamine, diethylamine, diisopropylamine, ethanolamine, triethylamine, 3-amino-1-propanol and the like.

A80789 acyl ester derivatives are prepared by treating A80789 with a corresponding acid anhydride or acid chloride. Esterification occurs at one of the A80789 hydroxyl groups. Such esters are typically prepared by reacting A80789 with, for example, the corresponding acid anhydride at room temperature.

Preferred A80789 acyl ester derivatives are those where a hydrogen atom of one or more of the hydroxyl groups is replaced by acetyl, propionyl, isobutyryl or butyryl.

A80789 alkyl ester derivatives are prepared by esterification of the carboxyl group, using standard procedures. The preferred alkyl esters are methyl, ethyl, propyl, isopropyl, and the butyl esters. The A80789 alkyl ester derivatives are typically less active when tested in vitro. When administered to an animal, however, such esters can act as pro-drugs which are converted to A80789 in vivo.

Preferred A80789 ether derivatives are those compounds wherein Y represents O. The ether derivatives are prepared by reacting A80789, or a salt thereof, with a corresponding primary alcohol or thiol.

With some of the starting alcohols or thiols it may be necessary to add an acid catalyst to the reaction. Suitable catalysts include hydrochloric acid, sulfuric acid, methanesulfonic acid, benzenesulfonic acid, toluenesulfonic acid, selenium dioxide, and boron trifluoride.

A solvent such as, for example, water, acetone, benzene, ether, tetrahydrofuran, or dioxane may be added to facilitate the reaction. Reactions generally occur at room temperature, although higher temperatures may be used.

Although ordinary reaction work-up procedures are sometimes sufficient, additional purification may be required to obtain the compounds of this invention. Such purification may be accomplished by well-known methods, such as, for example, column chromatography, thin-layer chromatography, fractional crystallization and the like.

The A80789 compounds have antibacterial and anticoccidial activity. A80789 compounds are especially active against anaerobic bacteria. The minimal inhibitory concentrations (MIC's) at which A80789 inhibits various bacteria, as determined by standard agar-dilution assays, are summarized in Tables III and IV. End points were read after 24-hour incubation.

TABLE III

In Vitro Antibacterial Activity of Antibiotic A80789

| Test Organism | MIC (mcg/mL) |
| --- | --- |
| *Staphylococcus aureus* X1.1 | .25 |
| *Staphylococcus aureus* V41 | .25 |
| *Staphylococcus aureus* X400 | .25 |
| *Staphylococcus aureus* S13E | .25 |
| *Staphylococcus epidermidis* Epi 1 | .25 |
| *Staphylococcus epidermidis* 222 | .125 |
| *Streptococcus pyogenes* C203 | .03 |
| *Streptococcus pneumoniae* Park 1 | .03 |
| *Streptococcus faecium* X66[a] | >128 |
| *Streptococcus faecalis* 2041[b] | >128 |
| *Haemophilus influenzae* C.L. | >128 |
| *Haemophilus influenzae* 76 | >128 |
| *Escherichia coli* N10 | >128 |
| *Escherichia coli* EC14 | >128 |
| *Escherichia coli* TEM | >128 |
| *Enterobacter aerogenes* C32 | >128 |
| *Enterobacter aerogenes* EB17 | >128 |
| *Klebsiella* sp. | >128 |
| *Salmonella* sp | >128 |
| *Pseudomonas aeruginosa* X528 | >128 |
| *Pseudomonas aeruginosa* X239 | >128 |
| *Pseudomonas aeruginosa* PS18 | >128 |
| *Pseudomonas aeruginosa* PS72 | >128 |
| *Serratia marcescens* X99 | >128 |
| *Proteus* sp. | >128 |
| *Shigella sonnei* | >128 |

[a]Reclassified as *Enterococcus faecium* X66
[b]Reclassified as *Enterococcus faecalis* 2041

TABLE IV

Susceptibility of Anaerobic Bacterial Isolates to Antibiotic A80789

| Anaerobic Bacteria | MIC (mcg/mL) |
| --- | --- |
| Clostridium difficile 2994 | .5 |
| Clostridium perfringens 81 | .5 |
| Clostridium septicum 1128 | .5 |
| Eubacterium aerofaciens 1235 | .5 |
| Peptococcus asaccharolyticus 1302 | $\leq$.03 |
| Peptococcus prevoti 1281 | .125 |
| Peptostreptococcus anaerobius 1428 | .25 |
| Peptostreptococcus intermedius 1264 | .125 |
| Propionibacterium acnes 79 | .25 |
| Bacteroides fragilis 111 | 8 |
| Bacteroides fragilis 1877 | 8 |
| Bacteroides fragilis 1936B | 8 |
| Bacteroides thetaiotaomicron 1438 | 128 |
| Bacteroides melaninogenicus 1856/28 | 4 |
| Bacteroides melaninogenicus 2736 | 8 |
| Bacteroides vulgatis 1211 | 1 |
| Bacteroides corredens 1874 | 8 |
| Fusobacterium symbiosum 1470 | 2 |
| Fusobacterium necrophorum 6054A | 2 |

Anticoccidial activity is an important property of the A80789 compounds. For example, in an in vitro tissue-culture screen against *Eimeria tenella*, A80789 was active at 0.31 mcg/mL. As demonstrated by feeding experiments, the presence of antibiotic A80789 in the feed of young chickens at levels as low as 100 ppm caused a reduction in the number of lesions in chicks infected with *Eimeria acervulina*.

In another aspect, this invention relates to compositions for treating coccidiosis. These compositions consist of an A80789 compound combined with a physiologically acceptable carrier. For treating coccidiosis in poultry, an A80789 compound is most conveniently supplied in an anticoccidial amount with the feed ingested by the birds. The rates of administration of the A80789 compound are generally in the range of about 2 to 200 ppm in the feed and are preferably in the range of about 25 to 100 ppm of feed ration.

Another important property of the A80789 compounds is the ability to improve feed-utilization efficiency in animals. For example, the A80789 compounds improve feed-utilization efficiency in ruminants which have a developed rumen function. The efficiency of feed use can be monitored by observing the production and concentration of propionate compounds in the rumen using the method described by Arthur P. Raun in U.S. Pat. No. 3,839,557. The A80789 compounds are typically effective in increasing propionates and, thereby, the efficiency of feed utilization when administered to ruminants orally at rates of from about 0.02 mg/kg/day to about 1.5 mg/kg/day. Preferable rates of administration are from about 0.05 mg/kg/day to about 0.5 mg/kg/day.

This invention further relates to feed compositions adapted to increase feed utilization comprising feed ration and from about 2 to 40 grams per ton of an A80789 compound.

As described supra, A80789 compounds are active against anaerobic bacteria, including *Clostridium perfringens*. A80789 compounds should, therefore, be beneficial in the treatment or prevention of enteritis in chickens, swine, cattle and sheep, or the treatment of enterotoxemia in ruminants.

A80789 also has antiviral activity. For example, tissue-culture tests show that A80789 is active against Herpes (HSV I and II), Vaccina, Great Lakes influenza, Para influenza, and Rhino viruses at a level of 2 mg/mL and Pseudorabies virus at <0.078 mcg/mL.

The A80789 compounds can be administered to animals orally or parenterally. The most practical way to administer the A80789 compounds for treatment of coccidiosis or as an agent to increase feed-utilization efficiency is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses, or capsules. Each individual dosage unit should contain a quantity of A80789 compound directly related to the proper daily dose for the animal to be treated.

The methods of formulating drugs into animal feeds are well known. A preferred method is to make a concentrated drug premix which in turn is used to prepare medicated feeds. An A80789 compound can be formulated as a feedstuff premix. The term "feedstuff premix" means a composition of an A80789 compound in combination with a suitable edible carrier, diluent, or excipient, and if desired suitable binders, antidust agents, and the like. Such a mixture of the carrier and the A80789 compound will preferably contain about 5 to 90 percent by weight of the A80789 compound, and preferably about 10 to 70 percent by weight. Typical premixes may contain from about 1 to about 200 grams of drug per pound of premix. Premixes may be either liquid or solid preparations.

The final formulation of feeds for animals will depend upon the amount of drug to be administered. The common methods of formulating, mixing, and pelleting feeds may be used to prepare feeds containing an A80789 compound.

The A80789 compounds may be formulated for parenteral administration by methods recognized in the veterinary pharmaceutical art. Effective injectable compositions containing the A80789 compounds may be in either suspension or solution form. In the solution form, the A80789 compound is dissolved in a physiologically acceptable carrier. Such carriers comprise a suitable solvent, preservatives such as benzyl alcohol, if needed, and buffers. Useful solvents include, for example, alcohols, glycols, or inert oils such as vegetable oils or highly refined mineral oils.

Injectable suspension compositions are prepared using a nonsolvent for the compound with adjuvants, as a carrier. The nonsolvent can be, for example, water or a glycol such as polyethylene glycol.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the liquid nonsolvent can assist in making injectable suspensions in individual cases. For example, silicone antifoams, glycols, sorbitol, and sugars can be useful suspending agents.

The A80789 compounds are also useful as insecticides. For example, A80789 is active against adult housefly at levels as low as 100 ppm.

A80789 Combinations

Previously, a number of compounds were found to have an advantageous effect on the anticoccidial activity of one or more polyether antibiotics. For example, synergistic anticoccidial combinations comprising nicarbazin or 4,4'-dinitrocarbanilide and polyether antibiotics were disclosed by M. E. Callender and T. K. Jeffers in U.S. Pat. No. 4,218,438. A. J. Clinton and G. O. P. O'Doherty found that certain naphthalenamines and benzenamines had a beneficial effect on the anticoccidial activity of some polyether antibiotics (See U.S. Pat. Nos. 4,764,534 and 4,366,168, respectively).

Nicarbazin and 4,4'-dinitrocarbanilide are described in U.S. Pat. No. 2,731,382. Nicarbazin is a complex of 4,4'-dinitrocarbanilide and 2-hydroxy-4,6-dimethylpyrimidine, but the 4,4'-dinitrocarbanilide alone exhibits anticoccidial activity [See *Science*, 122: 244 (1955)].

Thus, another group of compositions of this invention are combinations for controlling coccidiosis in poultry comprising:
1) an A80789 compound in combination with
2) a compound selected from the group consisting of
   a) nicarbazin,
   b) 4,4'-dinitrocarbanilide,
   c) a naphthalenamine compound of formula 2:

2 wherein:
$R^2$ is $C_1$-$C_4$ alkyl;
$R^3$ is halogen, $C_1$-$C_4$ fluoroalkyl, $C_1$-$C_4$ fluoroalkoxy or $C_1$-$C_4$ fluoroalkylthio;
$R^4$ is halogen;
$R^5$ is hydrogen or halogen;
m is 0, 1 or 2; and
n is 0 or 1;
with the proviso that, when an $R^4$ substituent exists, it is at other than the 2-position;
d) a benzenamine selected from 2,4-dinitro-N-[4-(trifluoromethoxy)phenyl]-6-(trifluoromethyl)benzenamine; 2,4-dinitro-N-[4-(1,1,2,2-tetrafluoroethoxy)phenyl] -6-(trifluoromethyl)benzenamine or 2,4-dinitro-N-[4-(pentafluoroethoxy)phenyl]-6-(trifluoromethyl)benzenamine; or
e) a pharmaceutically acceptable salt of a (b)–(d) compound.

The methods of synthesis of the naphthalenamine compounds and the preferred compounds of this group were disclosed by A. J. Clinton and G. O. P. O'Doherty in U.S. Pat. No. 4,764,534.

The components of the combinations of an A80789 compound with compounds 2(a)–(d) are used in amounts which, in combination, are microbiologically active against at least one coccidiosis-causing organism. In general, the maximum amounts to be used in the combinations are the same as the maximum amounts for anticoccidial treatment by the individual components. The lower limits are generally less than that required for therapy by the individual components. Accordingly, the present invention includes feed compositions containing 1) from about 2 to about 100 ppm of an A80789 compound and 2) a) from about 5 to 125 ppm of nicarbazin, b) from about 25 to about 150 ppm of 4,4'-dinitrocarbanilide, c) from about 1 to about 1000 ppm of a naphthalenamine, or d) from about 1 to about 125 ppm of a benzenamine. The A80789 compounds are particularly effective when administered with a benzenamine, naphthalenamine or nicarbazin. Feed compositions of the preferred combinations contain from about 2 to about 20 ppm of an A80789 compound with from about 5 to about 80 ppm of a benzenamine, naphthalenamine or nicarbazin.

This invention also relates to the combinations defined above formulated as a feedstuff premix. This premix is a composition consisting of a combination of the first component, an A80789 compound, and the second component, a 2(a)–(d) compound, combined with a suitable edible carrier. This composition will contain about 5 to 90 percent by weight of the anticoccidial combination, preferably about 10 to 70 percent by weight.

In order to illustrate more fully the operation of this invention, the following examples are provided:

EXAMPLE 1

Preparation of A80789

A. Shake-flask Fermentation of A80789

The culture *Streptomyces hygroscopicus* NRRL 18513, either as a lyophilized pellet or as a suspension maintained in liquid nitrogen, was used to inoculate a seed medium having the following composition:

| Seed Medium | |
|---|---|
| Ingredient | Amount (%) |
| Glucose | 1.0 |
| Soluble starch | 2.0 |
| Yeast extract | 0.5 |
| Enzymatic hydrolysate of casein* | 0.5 |
| $CaCO_3$ | 0.1 |
| Deionized water | q.s. 1 liter |
| Unadjusted pH=6.6; add NaOH to raise the pH to 7.2 before sterilizing; post-sterilization pH=6.8. | |

*NZ Amine A (Sheffield Chemical Co., Norwich, N.Y.)

Slants or plates were prepared by adding 2% agar to the seed medium. The inoculated slant was incubated at 30° C. for from about 10 to about 14 days. The mature slant culture was scraped with a sterile tool to loosen the spores and the mycelial mat was removed. About one-fourth of the loosened spores were used to inoculate 50 mL of a vegetative medium of the same composition as the seed medium.

The inoculated vegetative medium was incubated in a 250-mL Erlenmeyer flask at 30° C. for about 72 hours on a shaker orbiting in a two-inch (5.08 cm) circle at 250 rpm.

This incubated vegetative medium (0.4 mL) was used to inoculate 50 mL of a second-stage vegetative medium having the same composition as that of the vegetative medium.

The inoculated second-stage vegetative medium was incubated in a 250-mL wide-mouth Erlenmeyer flask at 30° C. for 10 to 12 days on a shaker orbiting in a two-inch circle at 250 rpm.

B. Tank Fermentation of A80789

In order to provide a larger volume of inoculum, 10 mL of incubated vegetative medium, prepared as described in Section A, was used to inoculate 400 mL of a second-stage vegetative medium having the same composition as that of the vegetative medium. This second-stage vegetative medium was incubated in a 2-L wide-mouth Erlenmeyer flask for about 48 hours at 30° C. on a shaker orbiting in a two-inch circle at 250 rpm.

This incubated second-stage vegetative medium (800 mL) was used to inoculate 115 L of sterile production medium having the following composition:

| Production Medium | |
|---|---|
| Ingredient | Amount (/L) |
| Blackstrap molasses | 20.0 g |
| Glucose | 10.0 g |
| Peptone[a] | 5.0 g |
| CaCO$_3$ | 2.0 g |
| Czapek's mineral stock[b] | 2.0 ml |
| Deionized water | q.s. to 110 L |
| Unadjusted pH=6.9; no pH adjustment; post-sterilization pH=7.0 | |
| Antifoam added: Sag 471[c] (.2 g/L) and P-2000[d] (0.5 mL/L) | |

[a]Bacto Peptone (Difco Laboratories, Detroit, MI)
[b]Czapek's Mineral Stock has the following composition:
KCl 10%
MgSO$_4$.7H$_2$O 10%
FeSO$_4$.7H$_2$O 0.2%
(Dissolved in 2ml of conc. HCl)
Deionized Water q.s. to 1 L
[c]Sag 471 (Union Carbide, Sistersville, WV)
[d]P-2000 (Dow Chemical Co., Midland, MI)

The inoculated production medium was allowed to ferment in a 165-L stirred fermentation tank for 4 to 5 days at a temperature of 30° C. A dissolved oxygen level above 40% of air saturation was maintained with low airflow (0.25 v/v/m) and 150–300 rpm in the stirred vessel.

EXAMPLE 2

Isolation of A80789

Whole fermentation broth from two 100-L tanks, prepared in a manner similar to that described in Example 1, were combined (200 L) and filtered through a filter press, using diatomaceous earth as a filter aid (3% Hyflo Super-Cel, Manville Products Corp., Lompoc Calif. 93436) to yield 162 L of filtrate.

The mycelial filter cake was extracted twice with acetone (40 L each). The acetone extracts were combined and concentrated in vacuo to a volume of about 20 L. This concentrate was combined with the broth filtrate. This mixture was adjusted to pH 9 with 5N NaOH, and the resulting solution was extracted with ⅔ volume of ethyl acetate. The ethyl acetate extract was concentrated in vacuo to a residue.

This residue was dissolved in toluene (250 mL), and the solution was applied to a column containing 2 L of silica gel (Woelm, 70–150 mesh) packed in toluene. The column was washed with toluene (10 L) and developed with toluene:ethanol [sequentially with 10 L each of (98:2) and (96:4)], collecting 1-L fractions.

Elution of A80789 was monitored by bioassay using *Bacillus subtilis* and by TLC [silica-gel plates (Merck), ethyl acetate, detection with bioassay or vanillin/H$_2$SO$_4$ spray, R$_f$=0.55]. Fractions containing most of the A80789 (#15-20) were combined and concentrated to an oil. This oil was dissolved in dioxane (50 mL) and freeze dried to yield crude A80789, also as an oil.

The crude A80789 was dissolved in chloroform (250 mL) and applied to a column containing 2 L of silica gel (Woelm, 70-150 mesh) packed in chloroform. The column was washed with chloroform (10 L) and with chloroform: acetone [sequentially with 10 L each of (97.5:2.5), (95:5) and (9:1)] and then with acetone (10 L), collecting 1-L fractions.

Elution was monitored by bioassay and TLC. Fractions containing most of the A80789 (#19-29) were combined and concentrated to an oil. This oil was dissolved in dioxane (100 mL) and freeze dried to give A80789 (Na salt) as an oil or solid.

This residue was dissolved in acetone (300 mL) and water (100 mL) was added. The pH of the solution was adjusted to 3.0 with 1N HCl, and additional water (200 mL) was added. The mixture was stirred for 15 minutes, whereupon a precipitate formed.

This precipitate was filtered, dissolved in acetone (300 mL), and water (300 mL) was added to induce crystallization. The crystals were filtered and dried in vacuo to yield 2.6 g of A80789 as a white powder (mp 115°–117° C.).

EXAMPLE 3

Preparation of A80789 (Na salt)

Whole fermentation broth from a 10-L tank was processed as described in Example 2. The fractions containing A80789 from the second silica-gel column were combined and concentrated in vacuo to a residue. This residue was dissolved in dioxane (50 mL) and freeze dried to yield 387 mg of A80789 sodium salt (mp 187°–189° C.).

EXAMPLE 4

Preparation of A80789 (free acid)

A80789 (Na salt, 150 mg), obtained as described in Examples 2 and 3, was dissolved in acetone (100 mL). Water (100 mL) was added to this solution; the pH of the resulting solution was adjusted to pH 3 by addition of 0.1N HCl, whereupon a precipitate formed. This precipitate was dissolved in acetone (50 mL), and water (50 mL) was added, whereupon crystallization occurred. The crystals were filtered and dried in vacuo to yield 113 mg of A80789 (mp 118°-120° C.).

EXAMPLE 5

Chromatographic Identification of A80789

TLC

| Absorbent: | silica gel | |
|---|---|---|
| Detection: | *Bacillus subtilis*; vanillin-H$_2$SO$_4$ spray | |
| System | | R$_f$ |
| Ethyl acetate | | .55 |
| Ethyl acetate/diethylamine (95:5) | | .52 |

II. Paper Chromatography

| Absorbent: | Whatman #1 paper |
|---|---|

| Detection: | *B. subtilis* |
|---|---|
| System | $R_f$ |
| .06M $(NH_4)_2HPO_4$, pH 7.1 | .39 |
| n-PrOH:$H_2O$ (1:9) | .84 |
| BuOH:EtOH:$H_2O$ (13.5:15:150) | .9 |

EXAMPLE 6

Preparation of 29-O-Methyl-A80789 Methyl Ester

Figure 3:
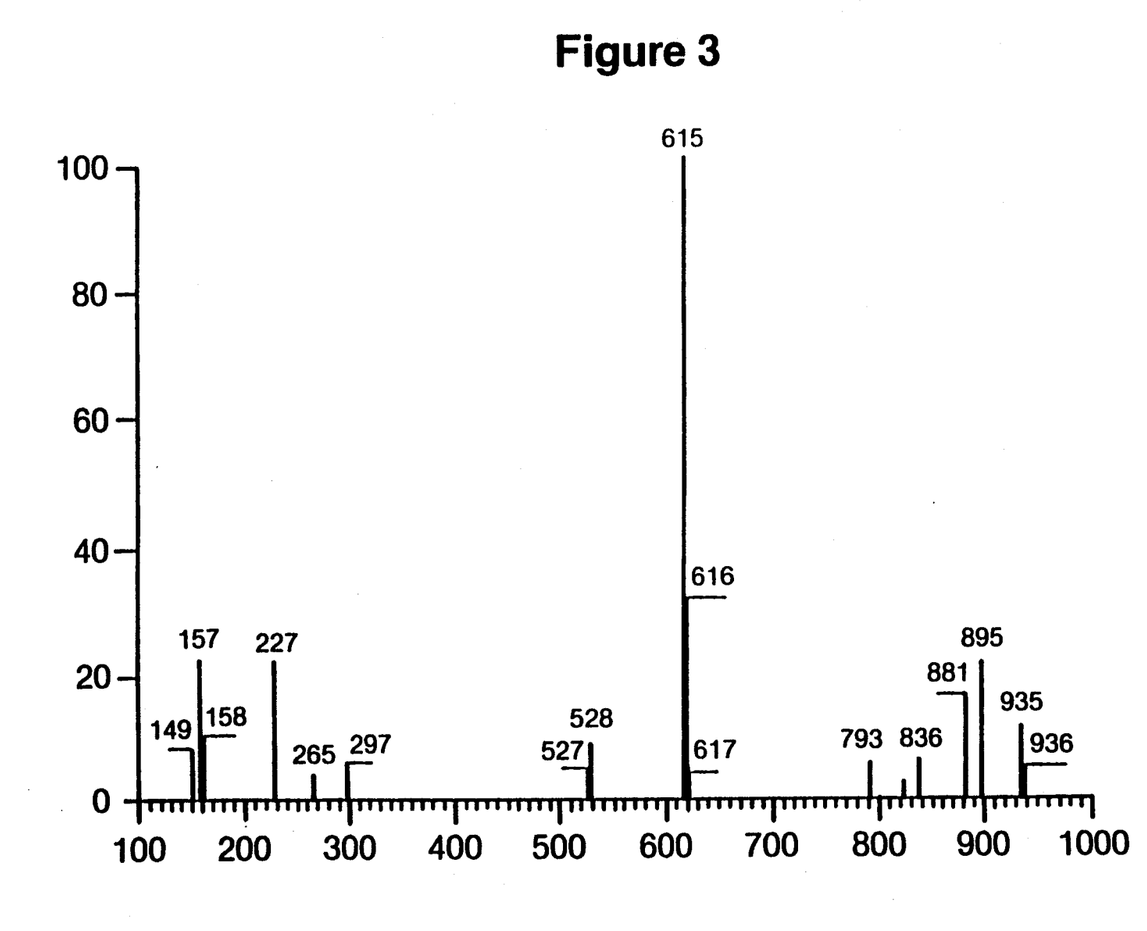
FIG. 3 shows the field desorption mass spectrum of 29-methyl ether-A80789 methyl ester.

A80789 was dissolved in MeOH and allowed to stand at room temperature for 18 hours. This solution was treated with a solution of diazomethane in diethyl ether. The resulting solution was concentrated in vacuo to give the title compound (see FIG. 3 for FD mass spectrum).

EXAMPLE 7

A typical modified chick ration for the control of coccidiosis is prepared using the following formula:

| Ingredients | Percent |
|---|---|
| Ground yellow corn | 50.0 |
| Soybean oil meal, extracted, dehulled (50%) | 30.89 |
| Animal fat | 6.5 |
| Fish meal with solubles (60%) | 5.0 |
| Corn distillers dried solubles | 4.0 |
| Dicalcium phosphate, feed grade | 1.8 |
| Calcium carbonate (ground limestone) | 0.8 |
| Vitamin premix TK-1 (1.03)[1] | 0.5 |
| Salt (NaCl) | 0.3 |
| Trace mineral premix TK-01 (1.02)[2] | 0.1 |
| Methionine hydroxy analog | 0.1 |
| A80789 (Na salt) | 0.01 |
| Total | 100.0 |

[1]Vitamin premix provides 3000 IU of Vitamin A, 900 IU of Vitamin D, 40 mg of Vitamin E, 0.7 mg of Vitamin K, 100 mg of choline, 70 mg of niacin, 4 mg of pantothenic acid, 4 mg of riboflavin, 0.1 g of Vitamin $B_{12}$, 0.1 of biotin and 125 mg of ethoxyquin per kg of complete feed.
[2]Trace mineral premix provides 75 mg of manganese, 50 mg of zinc, 25 mg of iron and 1 mg of iodine per kg of complete feed.

These substances are mixed in accordance with standard feed-mixing techniques. Chicks fed such a ration are protected against exposure to coccidiosis; weight gains are comparable to those of coccidiosis-free chicks fed a similar, unmedicated diet.

EXAMPLE 8

A balanced high-grain beef-cattle ration is prepared as follows:

| Ingredient | Percent |
|---|---|
| Finely ground corn | 67.8 |
| Ground corn cob | 10 |
| Dehydrated alfalfa meal, 17% protein | 5 |
| Soybean meal, solvent extracted, dehulled (50%) | 9.9956 |
| Cane molasses | 5 |
| Urea | 0.6 |
| A80789 (Na salt) | 0.0044 |
| Dicalcium phosphate, feed grade | 0.5 |
| Calcium carbonate | 0.5 |
| Sodium chloride | 0.3 |
| Trace mineral premix | 0.03 |
| Vitamin A and $D_2$ premix* | 0.07 |
| Vitamin E premix** | 0.05 |
| Calcium propionate | 0.15 |

*Containing per pound: 2,000,000 I.U. of Vitamin A; 227,200 IU of Vitamin $D_2$ and 385.7 g of soybean feed with 1% oil added
**Corn distillers dried grains with solubles containing 20,000 IU of d-alphatocopheryl acetate per pound This mixed feed is compressed into pellets. At an average daily ingestion rate of 15 pounds of feed per animal, this supplies approximately 300 mg of A80789 (Na salt) per animal per day.

We claim:

1. A process for producing antibiotic A80789 of the formula which comprises cultivating *Streptomyces hygroscopicus* NRRL 18513, or an A80789-producing mutant thereof, in a culture medium containing assimilable sources of carbon, nitrogen, and inorganic salts under submerged aerobic fermentation conditions until a substantial level of antibiotic A80789 is produced by said microorganism in said culture medium.

2. The process of claim 1 which includes the additional step of separating A80789 from the culture medium.

3. The process of claim 1 wherein *Streptomyces hygroscopicus* NRRL 18513, is used.

4. A biologically pure culture of *Streptomyces hygroscopicus* NRRL 18513, or an A80789-producing mutant thereof, said microorganism being capable of producing the antibiotic of the formula:

in recoverable quantity upon cultivation in an aqueous nutrient medium containing assimilable sources of carbon, nitrogen, and inorganic salts.

5. The culture of claim 4 which is *Streptomyces hygroscopicus* NRRL 18513.

* * * * *